United States Patent [19]

Jang

[11] Patent Number: 5,203,338

[45] Date of Patent: Apr. 20, 1993

[54] VASCULAR CATHETER HAVING LOW-PROFILE DISTAL END

[75] Inventor: Yue-Teh Jang, Fremont, Calif.

[73] Assignee: Cardiovascular Imaging Systems, Inc., Sunnyvale, Calif.

[21] Appl. No.: 930,977

[22] Filed: Aug. 14, 1992

Related U.S. Application Data

[63] Continuation of Ser. No. 629,500, Dec. 17, 1990, abandoned.

[51] Int. Cl.$^5$ .............................................. A61B 8/14
[52] U.S. Cl. ......................... 128/662.06; 128/663.01; 128/657; 128/4; 604/93; 604/160; 604/161; 604/280
[58] Field of Search ............... 604/93, 95, 264, 280, 604/282, 284, 22, 189, 40, 43, 44, 160, 161; 128/660.07, 662.03, 662.06, 663.01, 4–6, 657, 658

[56] References Cited

U.S. PATENT DOCUMENTS

| | | | |
|---|---|---|---|
| 4,217,904 | 8/1980 | Zahorsky | 604/268 |
| 4,735,606 | 4/1988 | Davison | 604/45 |
| 4,748,982 | 6/1988 | Horzewski et al. | 604/192 |
| 4,772,268 | 9/1988 | Bates | 604/43 |
| 4,794,931 | 1/1989 | Yock. | |
| 4,842,582 | 6/1989 | Mahurkar | 604/280 |
| 4,961,809 | 10/1990 | Martin | 604/43 |
| 5,024,234 | 6/1991 | Leary et al. | 128/662.06 |
| 5,054,492 | 10/1991 | Scribner et al. | 128/662.06 |
| 5,057,073 | 10/1991 | Martin | 604/43 |

OTHER PUBLICATIONS

EndoSonics Corporation, Rancho Cordova, Calif., CathScanner I System.
InterTherapy, Costa Mesa, Calif., InterTherapy Modular System Design.
Diasonics, Milpitas, Calif., Interventional Ultrasound System.
Medi-Tech, Inc., Watertown, Mass., designated Ultrasound Imaging Catheter Catalog No. 01-118.

*Primary Examiner*—C. Fred Rosenbaum
*Assistant Examiner*—Chalin Smith
*Attorney, Agent, or Firm*—Townsend and Townsend

[57] ABSTRACT

An ultrasonic imaging catheter comprises a catheter body having a distal region and proximal region. The distal region has a reduced cross-sectional area compared to that of the proximal region, and the proximal region includes at least two lumens therethrough for accommodating a movable guidewire and a rotatable working element, respectively. The catheter body may be inserted over the moveable guidewire, with the guidewire passing through a lumen in the distal region and the guidewire lumen in the proximal region. After positioning the catheter body, the guidewire can be retracted from the distal region and into the proximal region, leaving the lumen in the distal region available for the rotatable working element. Such a construction allows over-the-wire imaging of the catheter while minimizing the width of the catheter in the distal region which remains available for placement of the working element.

23 Claims, 3 Drawing Sheets

VASCULAR CATHETER HAVING LOW-PROFILE DISTAL END

This is a continuation of application Ser. No. 07/629,500 filed Dec. 17, 1990, now abandoned.

BACKGROUND OF THE INVENTION

1. Field of the Invention

The present invention relates generally to the construction and use of vascular catheters and, more particularly, to vascular catheters having a reduced-size distal tip capable of selectively receiving either a movable guidewire or a work element.

Arteriosclerosis, also known as atherosclerosis, is a common human ailment arising from the deposition of fatty-like substances, referred to as atheroma or plaque, on the walls of blood vessels. Such deposits occur both in peripheral blood vessels that feed limbs of the body and coronary blood vessels that feed the heart. When deposits accumulate in localized regions of the blood vessels, blood flow is restricted and the person's health is at serious risk.

Numerous approaches for reducing and removing such vascular deposits have been proposed, including balloon angioplasty, where a balloon-tipped catheter is used to dilitate a stenosed region within the blood vessel; atherectomy, where a blade or other cutting element is used to sever and remove the stenotic material; and laser angioplasty, where laser energy is used to ablate at least a portion of the stenotic material; and the like.

In order to more effectively apply such interventional techniques, a variety of vascular imaging devices and methods employed. Of particular interest to the present invention, intraluminal imaging catheters having ultrasonic transducers at their distal ends have been employed to produce images of the stenotic region from within the blood vessel.

A number of particular designs for such ultrasonic imaging catheters have been proposed. One approach has been to use a phased-array of discrete ultrasonic imaging transducers at the tip of a vascular catheter. While such an approach is advantageous in that it does not acquire mechanical manipulation of the transducers, it is problematic in that the image quality is limited. Such phased-array intravascular imaging catheters are commercially available from EndoSonics Corporation, Rancho Cordova, Calif., as the CathScanner I System.

A more promising approach for intravascular ultrasonic imaging employs mechanical rotation of the ultrasonic signal, either by mechanically rotating the transducer itself or by mechanically rotating a mirror which radially deflects the ultrasonic signal from the transducer. Such mechanical rotation generally provides a better image quality than use of a phased-array system, but the design of the catheters is problematic since the designs must provide for rotating the transducer and/or an associated mirror at speeds usually in the range from 500 to 2000 rpm. Moreover, the interior blood vessel must be protected from the rotating components which could cause substantial injury should they come in contact with the blood vessel.

A number of specific designs for mechanical ultrasonic imaging catheters have been described. An early design is illustrated in U.S. Pat. No. 4,794,931, where the mechanical components of the imaging system are located within a housing at the distal end of the catheter. The housing includes a fixed guidewire at its distal tip which is used to position the catheter within the vascular system. While the use of such fixed-guidewire designs can provide an excellent image quality, under some circumstances it is desirable to use an "over-the-wire" design where the catheter may be introduced over a separate (movable) guidewire. The use of a movable guidewire has certain advantages including improvement in steering capability through branch coronary arteries and elsewhere and facilitating catheter exchange, e.g. substitution of an interventional catheter after the imaging has been completed.

A particular design for an over-the-wire ultrasonic imaging catheter is illustrated in FIG. 1. The catheter includes the catheter body 10 having an exterior catheter lumen 12 attached near its distal end. A rotatable ultrasonic imaging assembly 14 is mounted at the distal end of the drive member 16, and the device may be introduced over a conventional movable guidewire 18, as illustrated. Such designs employing parallel lumens, however, are disadvantageous since the width of the distal tip in the region of the ultrasonic imaging element must be sufficient to also accommodate the guidewire. Ideally, to be able to cross very narrow lesions, the diameter of the catheter in the region of the imaging element should be minimized, preferably including only the imaging element to be rotated and a catheter sheath surrounding the imaging element. The requirement of the separate guidewire lumen increases this minimum size, making the design unsuitable for small blood vessel type lesions and for passing through conventional guiding catheters.

Designs of the type illustrated in FIG. 1 are commercially available from Medi-Tech, Inc., Watertown, Mass. A design similar to that of FIG. 1 is illustrated in copending application Ser. No. 07/422,935, the disclosure of which is incorporated herein by reference.

An alternative design for a mechanical ultrasonic imaging catheter avoids the requirement for a parallel guidewire lumen by providing for exchange of the mechanical imaging components with a conventional guidewire. As illustrated in FIG. 2, such a catheter comprises a single lumen catheter sheath 20 which can receive a drive wire 22 carrying an ultrasonic imaging assembly 24 at its distal end. The catheter sheath 20 may be initially introduced over a conventional guidewire. The guidewire may then be completely removed and replaced with the imaging assembly. While the diameter of the catheter 20 may be minimized, the need to exchange the guidewire and imaging components whenever the catheter is to be repositioned is time consuming and disadvantageous. Such catheters are commercially available from Inter-Therapy, Inc., Costa Mesa, Calif.

For these reasons, it would be desirable to provide ultrasonic imaging catheters which combine a narrow profile in the region of the ultrasonic imaging components and an ability to be introduced over a separate, moveable guidewire. It would be particularly desirable if such designs would allow for imaging within the narrow distal region of the catheter without the need to remove the guidewire from the catheter body. In particular, such imaging catheter should present a width of less than about 5 French, and more preferably being less than about 3 French, to facilitate entry into the coronary arteries and even very tight lesions.

SUMMARY OF THE INVENTION

According to the present invention, vascular catheters comprise a catheter body having a proximal end and a distal end. The catheter body includes at least a distal region extending proximally from its distal tip and a proximal region extending proximally from the proximal end of the distal region. The distal region has a reduced cross-sectional area compared to the proximal region, with the distal region typically including only a single lumen and the proximal region including at least a pair of parallel lumens.

The lumen in the distal region of the catheter body is contiguous with both of the parallel lumens in the proximal region. Thus, a drive shaft which is reciprocatably disposed in one of the lumens in the proximal region is able to be selectively advanced to the distal region or retracted back into the proximal region. The catheter body can be inserted over a guidewire by passing the guidewire through the lumen in the distal region into the other lumen at the proximal region, i.e., the lumen which is not occupied by the drive shaft. A work element, typically an ultrasonic imaging transducer, is mounted at the distal end of the drive shaft and can be moved in and out of the distal region by reciprocating the drive shaft.

In use, the catheter body can be introduced over a movable guidewire which has been previously positioned at a desired location within the vascular system. The catheter body is manipulated until the distal region lies within the location of interest, typically a steotic lesion. Once the catheter body is in position, the movable guidewire can be retracted (i.e. pulled in the proximal direction) so that it evacuates the lumen in the distal region but remains within a lumen in the proximal region. The work element on the drive shaft, typically an ultrasonic transducer, can then be advanced in the distal direction so that it enters the lumen in the distal region. Imaging or another interventional technique may then be performed using the work element, and, after completion, the work element may be retracted into its lumen within the proximal region. The guidewire can then be advanced through the distal region and the catheter body repositioned over the guidewire so that the distal region is moved to another location of interest.

Thus, the present invention provides an intravascular catheter which combines a distal region having a minimum cross-sectional area to facilitate entry into coronary arteries and very tight stenotic lesions with the ability to introduce the catheter over a movable guidewire and retain the guidewire in place during imaging or another interventional procedure.

DESCRIPTION OF THE PREFERRED EMBODIMENT

Figure 1:
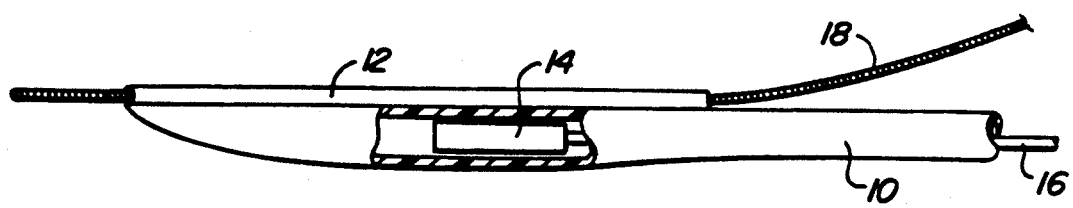
FIG. 1 illustrates a first catheter of the prior art.
Figure 2:
FIG. 2 illustrates a second catheter of the prior art.

Catheters constructed in accordance with the principles of the present invention will comprise an elongate catheter body having a proximal end and a distal end. The catheter body will include at least two regions, with a distal region extending from the distal tip of the catheter body to a location spaced proximally from the tip and a proximal region extending proximally from the proximal end of the distal region. The distal region will have a common lumen extending therethrough and a reduced cross-sectional area to facilitate entry into coronary blood vessels and/or tight stenotic lesions. The proximal region will have a somewhat larger cross-sectional area to accommodate at least two lumens extending therethrough, with a first lumen capable of receiving a conventional movable guidewire and a second lumen capable of receiving a working element attached to the distal end of a drive shaft. Both the first and second lumens connect to the common lumen in the distal region. Thus, the catheter body may be introduced to a blood vessel with the guidewire passing through the common lumen at the distal region and the first lumen in the proximal region. After the catheter body is in place, the movable guidewire may be retracted within the first lumen of the distal region and the working element advanced into the common lumen from the second lumen in the proximal region. The cross-sectional area of the distal region is thus minimized since it never has to simultaneously accommodate both the working element and the movable guidewire.

A catheter design of the present invention is expected to find its greatest use in the construction of ultrasonic imaging catheters used for intravascular imaging of blood vessels. In such cases, a working element will include an ultrasonic transducer having a focal length and operating at a frequency suitable for imaging within the dimensions of a blood vessel. Optionally, the ultrasonic transducer may be mounted in an assembly together with a reflective member (mirror), where the transducer emits and receives ultrasonic energy in a substantially axial direction and the mirror is oriented to deflect the emitted and received energy in the radial direction. The use of a mirror to deflect the ultrasonic energy increases the effective focal length at which the transducer operates, improving image quality. Space between the reflective element and the transducer eliminates "ring down" effect, thus improving image quality. The design and use of ultrasonic imaging transducers are described in U.S. Pat. Nos. 3,938,502; 4,576,177; and 4,794,931; disclosures of which are incorporated herein by reference.

In addition to ultrasonic transducers, the present invention is suitable for the construction of vascular catheters carrying a variety of other working elements, particularly rotatable working elements such as cutters, abraders, rotating mirrors for deflecting laser radiation, and the like. Catheters employing such working elements are described in U.S. Pat. Nos. 4,648,402;

4,669,469; and 4,631,052, the disclosures of which are incorporated herein by reference. The present invention may find use whenever the catheter employs a rotatable element which requires placement partially or wholly within a catheter sheath in order to protect blood vessel lining.

The catheter body will comprise one or more flexible tubular members having axial lumens formed therein, as described in more detail hereinbelow. A catheter body will be suitable for insertion into and manipulation within a patient's vascular system using techniques which are now well known in the medical community so that the distal region of the catheter body may be brought to a desired location within the vascular system.

The overall dimensions of the catheter will depend on use, with the length varying widely, typically being between about 40 cm and 150 cm, usually being between about 40 cm and 120 cm for peripheral catheters and being between about 110 cm and 150 cm for coronary catheters. The diameter of the catheter body may also vary widely, with the diameter of the distal region typically being between about 2 F (French) and 3 F, and the diameter of the proximal region typically being about 3 F and 6 F. A particular advantage of the catheter of the present invention is that the distal region may be made very small, with the lower limit on size typically being based on the diameter of the ultrasonic transducer or other working element which is being achieved. As the size of such working elements is further decreased with advancements in the art, it is expected that the diameter of the catheter body of the present invention may be made even smaller.

The catheter body may be composed of a wide variety of biologically compatible materials, typically being made from natural or synthetic polymers such as silicone rubber, natural rubber, polyvinylchloride, polyurethanes, polyesters, polyethylene, polytetrafluoroethylene (PTFE), and the like. Frequently, the catheter body may be formed as a composite having a reinforcement material incorporated within the elastomeric body in order to enhance strength, flexibility, and toughness. Suitable enforcement layers include wire mesh layers. The flexible tubular members of the catheter body will normally be formed by extrusion, with one or more integral lumens being provided. The catheter diameter can then be modified by heat expansion and shrinkage using conventional techniques. Particular techniques for forming the vascular catheters of the present invention are well described in the patent and medical literature.

The catheter body may be formed from a single tubular member which extends the entire distance from the proximal end to the distal end or may be formed from two or more tubular members which are joined together, either in tandem or in parallel. On the catheter bodies formed from a single tubular member, the proximal region will be expanded relative to the distal region and appropriate lumens will be formed in the interiors of the two regions. Alternatively, the distal region in the catheter body may be formed from a single tubular member having a single lumen while the proximal region is formed from a second tubular member having at least two axial lumens. The two regions may then be joined together so that the common lumen and the distal tubular element is contiguous with both the parallel axial lumens and the proximal region. As a second alternative, the catheter body may include a single tubular member having a single axial lumen which extends the entire length from the distal end to the proximal end. The proximal section is formed by securing a second tubular member to the side of the first tubular member and penetrating the first tubular member so that the respective lumens are made contiguous. The distal region of the catheter is that portion which remains forward of the point where the two tubes are joined.

The distal region of the catheter will typically have a length in the range from about 1 cm to 20 cm, more typically being in the range from about 2 cm to 10 cm, with the proximal region extending in the proximal direction from the distal region. The proximal region, however, need not extend the entire distance to the proximal end of the catheter body. It will often be desirable to extend the guidewire lumen formed by the proximal region only a portion of the distance from the distal region back toward the proximal end of the catheter body, typically extending from about 10 cm to 30 cm, more typically extending from 15 cm to 25 cm. In this way, the guidewire lumen can have a "monorail" design which facilitates exchange in the catheter over the guidewire. Such monorail designs are described generally in U.S. Pat. No. 4,748,982, the disclosure of which is incorporated herein by reference.

The width of the distal region will typically be below about 0.15 cm, usually being below about 0.13 cm, and frequently being below about 0.1 cm. The width of the proximal region will typically be above about 0.17 cm, and frequently being above about 0.2 cm. The width, of course, need not be uniform along the entire catheter length and some variation is permitted.

The drive shaft which is reciprocatably disposed within a lumen in the proximal region of the catheter will be flexible and suitable for transmitting torque from the proximal end of the catheter to the working element at its distal end. Depending on the application, the drive shaft may be a solid core wire, but will more typically have a braided construction. Suitable drive shaft constructions are described in copending application Ser. No. 07/500,818, the disclosure of which is incorporated herein by reference. In the case of an ultrasonic transducer as the working element, the drive shaft will also carry the necessary electrical leads for connecting the transducer.

Catheters according to the present invention will include a housing formed at the proximal end of the catheter body. The housing will seal the interior lumen of the catheter body which carries the drive shaft and will provide means for reciprocating the drive shaft axially within the catheter body. In the case of ultrasonic imaging catheters, the housing will also include the necessary electrical connection means for coupling the electrical leads on the drive shaft to the associated electronic imaging producing equipment. The drive shaft will further include a spindle or other means for coupling the drive shaft to an electric drive motor for rotating the ultrasonic transducer or other working element. Suitable spindles and drive motors are illustrated in U.S. Pat. No. 4,771,774, the disclosure of which is incorporated herein by reference.

Figure 3:
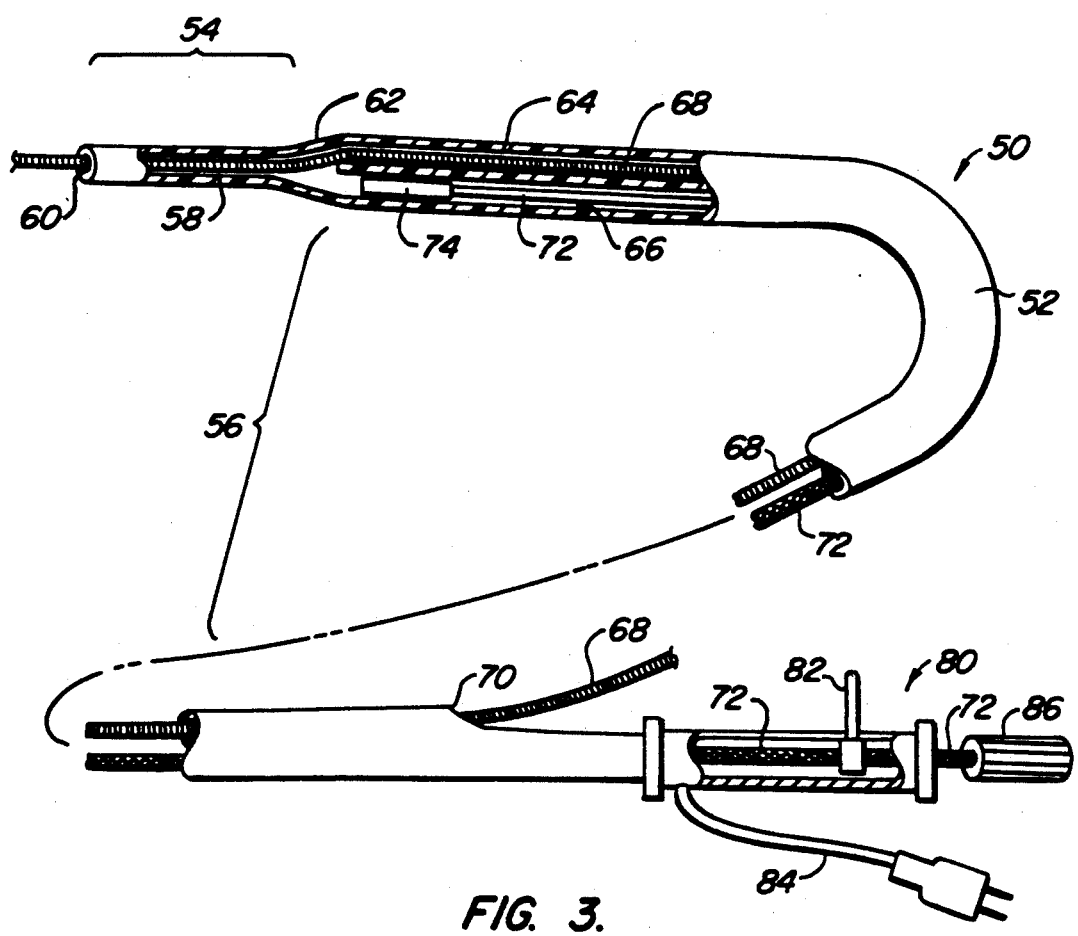
FIG. 3 illustrates a catheter constructed in accordance with the principles of the present invention.

Referring now to FIG. 3, a first embodiment 50 of the catheter of the present invention is illustrated. The catheter 50 includes a flexible catheter body 52 having a distal region 54 and a proximal region 56. The distal region 54 includes a single lumen 58 which extends from a distal port 60 to a transition region 62. The proximal region 56 includes a first lumen 64 and second lumen 66.

The first lumen 64 carries a movable guidewire 68 which, as illustrated, extends from a proximal port 70 through the lumen 58 and in distal region 54 and out the distal port 60. In this way, a catheter 50 can be inserted over the guidewire 68 in a conventional manner.

Figure 4:
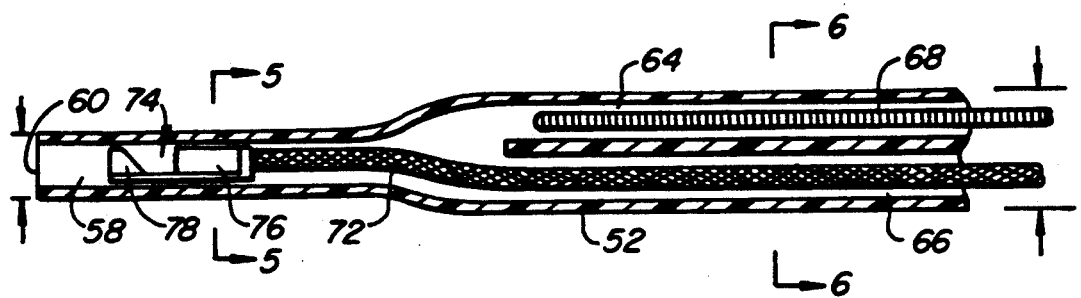
FIG. 4 is an enlarged drawing of the distal end of the catheter of FIG. 3, shown with the work element advanced into the distal region.
Figure 5:
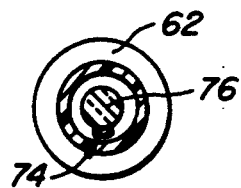
FIG. 5 is a cross-sectional view taken along line 5—5 in FIG. 4.
Figure 6:
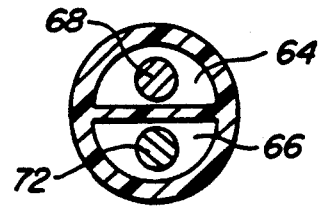
FIG. 6 is a cross-sectional view taken along line 6—6 in FIG. 4.

Drive shaft 72 is reciprocatably disposed within the second lumen 66. As illustrated in FIG. 3, ultrasonic imaging assembly 74 is secured to the distal end of the drive shaft 72 and remains within the proximal region 56 when the guidewire 68 extends into lumen 58 of the distal region 54. As illustrated in FIG. 4, however, once the guidewire 68 is retracted into the first lumen 64, the ultrasonic imaging assembly 74 may be advanced axially forward into the lumen 58 of the distal region 54.

In the preferred embodiment, the ultrasonic imaging assembly 74 includes an ultrasonic transducer 76 (FIG. 4) which is oriented to emit ultrasonic energy in the axially forward direction, and a mirror 78 which is disposed to deflect the ultrasonic energy from transducer 76 in a generally radial direction. The ultrasonic transducer 76 and mirror 78 are fixedly mounted relative to each other within the assembly 74 so that they will rotate together as the drive shaft 72 is rotated.

Catheter 50 further includes a proximal housing 80 secured to the proximal end of the catheter body 52. Proximal housing 80 includes a lever 82 which is attached to the drive shaft 72 which permits the user to selectively reciprocate the ultrasonic imaging assembly 74 between its retracted position (as illustrated in FIG. 3) and its extended position (illustrated in FIG. 4.) The ultrasonic imaging assembly 74 would normally be utilized only when it is in its extended configuration. It will be retracted when the catheter 50 is being positioned over the movable guidewire 68.

The housing 80 further includes an electrical connector plug 84 for coupling the electrical leads on the drive shaft 72 to the necessary electrical instrumentation for producing the ultrasonic image and a spindle 86 at the proximal terminal end of the drive shaft 72 for coupling to a motor drive, as described hereinabove. Conveniently, rings and commutators (not shown) may be provided in a conventional arrangement to couple electrical leads (not shown) from the transducer 76 (running along or through the drive shaft 72) to the connector plug 84.

Figure 7:
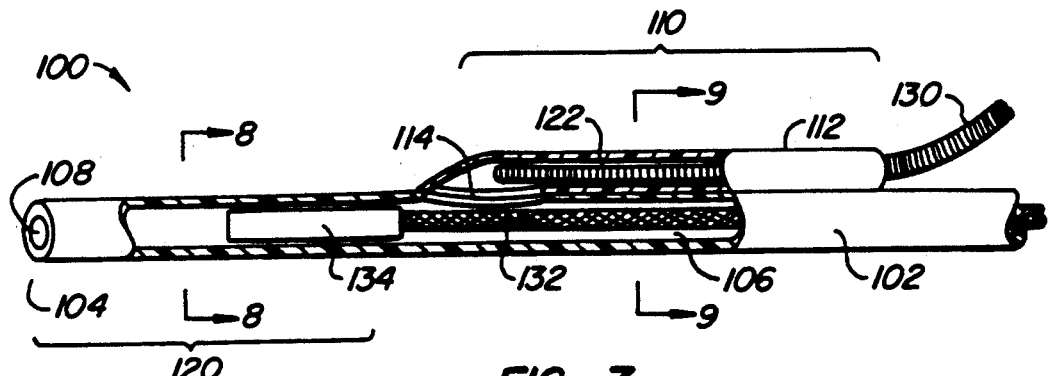
FIG. 7 illustrates an alternate construction of the catheter of the present invention.
Figure 8:
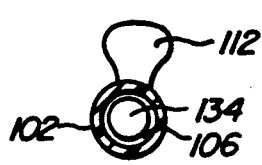
FIG. 8 is a cross-sectional view taken along line 8—8 in FIG. 7.
Figure 9:
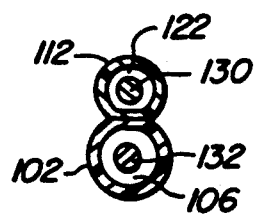
FIG. 9 is a cross-sectional view taken along line 9—9 in FIG. 7.

Referring now to FIGS. 7-9, an alternate embodiment 100 of the catheter of the present invention is illustrated. The catheter 100 includes a first flexible tubular member 102 which extends from a distal end 104 to a proximal end (not illustrated) of the catheter body. The first flexible tubular element defines a single lumen 106 which extends the entire length of the catheter body and terminates in a distal port 108. A proximal region 110 of the catheter 100 is defined by a second flexible tubular member 112 which is attached to the side of the first flexible tubular member 102 and which is interconnected with the lumen 106 of the first flexible tubular member through a port 114. A distal region 120 of the catheter 100 as defined as that region of the first flexible tubular member 102 which lies distally of the connecting port 114. Lumen 122 of the second flexible tubular member 112 is suitable for receiving a guidewire 130 in a conventional "monorail" fashion, while the lumen 106 of the first flexible tubular member 102 receives a drive shaft 132 having an ultrasonic imaging assembly 134 at its distal end. As illustrated in FIG. 7, the ultrasonic imaging assembly 134 lies within the distal region 120 of the catheter 100. The imaging assembly 134, of course, could be retracted to within the proximal region 110 of the catheter behind port 114. This way, the lumen 106 of the distal region 120 would be free to receive the advance of the guidewire 130 for positioning or repositioning of the catheter 100.

Figure 10:
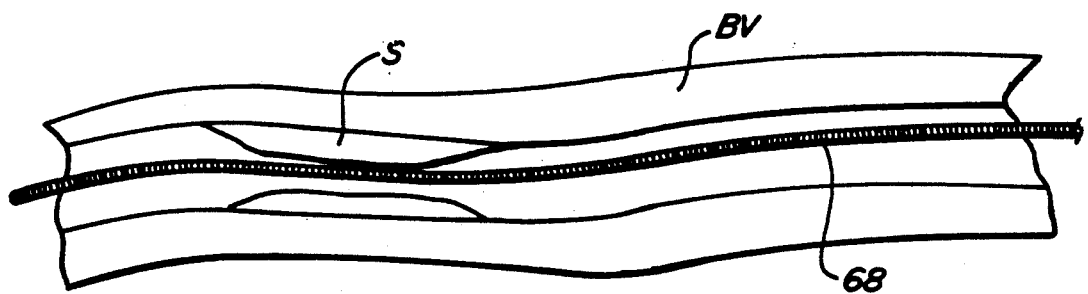
FIGS. 10-12 illustrate the method of the present invention using the catheter of FIGS. 1-6 to image a stenotic lesion.
Figure 11:
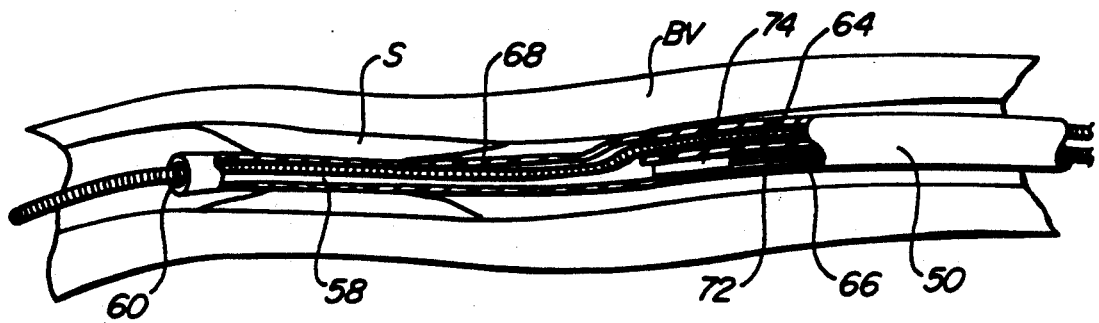
Figure 12:
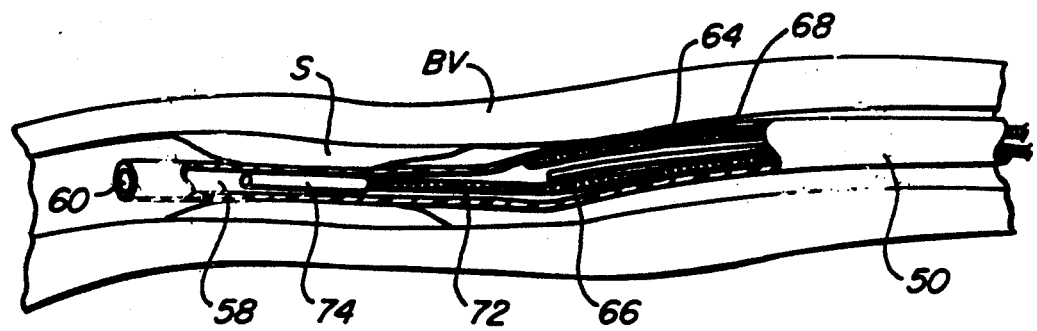

Referring now to FIGS. 10-12, use of the catheter 50 and guidewire 68 of FIG. 3 in positioning the catheter within a region of stenosis S within a blood vessel BV will be described. Initially, the guidewire 68 is introduced to the blood vessel in the conventional manner so that the distal end lies beyond the region of Stenosis, as illustrated in FIG. 10. After positioning of the guidewire 68, the catheter 50 is introduced over the guidewire by passing the proximal end of the guidewire 60 through distal port 60 and subsequently threading the guidewire through lumen 58 on the distal region 54 and lumen 64 in the proximal region 56. The catheter is advanced axially forward within the Blood Vessel until the proximal region 54 lies within the region of Stenosis. After the catheter 50 has been properly positioned, the ultrasonic imaging assembly 74 may be advanced to the position shown in FIG. 11 (or alternatively it may have been in such position while the catheter was being introduced to the Blood Vessel). After the imaging assembly 74 is located near the distal end of lumen 66, the guidewire 68 will be retracted in the distal direction until it is removed from lumen 58 in the distal region and lies wholly within lumen 64 within the proximal region 56. Once lumen 58 is cleared of a guidewire 68, the ultrasonic imaging assembly 74 may be advanced axially forward into the lumen 58, where it can then be used for imaging in a conventional manner.

At any time during the imaging procedure, the drive shaft 72 can be retracted to once again clear lumen 58. After clearing the lumen, the guidewire can again be advanced axially forward so that it is available for repositioning the catheter 50. Alternatively, the guidewire 68 may be left in place and the catheter 50 withdrawn over the guidewire so that it remains in place for different catheters to be introduced.

What is claimed is:

1. A vascular catheter comprising:
    a catheter body having a proximal end and a distal end, wherein the catheter body includes a proximal region having at least two lumens and a distal region having a single lumen which is connected to and in communication with both of the lumens in the proximal region and having a cross-sectional area which is less than the combined cross-sectional area of the two lumens of the proximal region;
    a drive shaft having a distal end and a proximal end and being reciprocatably disposed in one of the lumens in the proximal region of the catheter body; and
    a work element secured to the distal end of the driven shaft, whereby the work element may be extended into the single lumen in the distal region or retracted into the lumen in the proximal region by selectively reciprocating the drive cable.

2. A vascular catheter as in claim 1, wherein the work element is an ultrasonic imaging transducer.

3. A vascular catheter as in claim 1, wherein the work element is an assembly including an ultrasonic imaging transducer and a mirror arranged in tandem with the mirror oriented to deflect a signal from the transducer radially outward.

4. A vascular catheter as in claim 1, further comprising means at the proximal end of the catheter body for mechanically coupling the drive shaft to a motor drive and means for axially translating the drive shaft while it is being rotated.

5. A vascular catheter as in claim 1, wherein the distal region has a width less than about 0.15 cm and the proximal region has a width greater than about 0.15 cm.

6. A vascular catheter as in claim 1, wherein the single lumen is formed contiguously with the two lumens in the proximal region.

7. A vascular catheter as in claim 1, wherein the distal region and proximal region are formed from a single tubular member with the proximal region being expanded relative to the distal region.

8. A vascular catheter as in claim 1, wherein the distal region and proximal region are formed from separate tubular members which are joined together.

9. A vascular catheter as in claim 1, wherein the proximal region including both lumens extends fully to the proximal end of the catheter body.

10. A vascular catheter as in claim 1, wherein the second lumen of the proximal region does not extend fully to the proximal end of the catheter body.

11. A vascular catheter as in claim 1, wherein the catheter body includes a first tubular member having at least one lumen and extending from the distal end to the proximal end of the catheter body and a second tubular member having at least one lumen and secured to the side of the first tubular member, wherein the two lumens converge at a junction spaced proximally from the distal end of the catheter body whereby the distal region lies distal to the junction and the proximal region lies proximal to the junction.

12. A vascular catheter as in claim 11, wherein the second tubular member extends fully to the proximal end of the catheter body.

13. A vascular catheter as in claim 11, wherein the second tubular member does not extend fully to the proximal end of the catheter body.

14. A vascular imaging catheter system comprising:
a catheter body having a proximal end and a distal end, wherein the catheter body includes a proximal region having at least two lumens and a distal region having a single lumen which is connected to and in communication with both of the lumens in the proximal region and having a cross-sectional area which is less than the combined cross-sectional area of the two lumens of the proximal region;
a drive shaft having a distal end and a proximal end and being reciprocatably disposed in a first of the catheter body lumens;
an ultrasonic imaging transducer secured to the distal end of the drive shaft wherein the ultrasonic imaging transducer is mounted in a unitary assembly including a mirror arranged in tandem with the transducer and oriented to deflect a signal from the transducer radially outward; and
a guidewire slidably disposed in a second of the catheter body lumens;
whereby the catheter body may be introduced to a blood vessel over the guidewire and the guidewire and imaging transducer exchanged within the distal region of the catheter body by removing the guidewire from the proximal region of the catheter body and extending the imaging transducer into the distal region.

15. A vascular imaging catheter system as in claim 14, further comprising means at the proximal end of the catheter body for mechanically coupling the drive shaft to a motor drive and means for axially translating the drive shaft while it is being rotated.

16. A vascular imaging catheter system as in claim 14, wherein the distal region has a width less than about 0.15 cm and the proximal region has a width greater than about 0.15 cm.

17. A vascular imaging catheter system as in claim 14, wherein the single lumen is formed contiguously with the two lumens in the proximal region.

18. A vascular imaging catheter system as in claim 14, wherein the distal region and proximal region are formed from a single tubular member with the proximal region being expanded relative to the distal region.

19. A vascular imaging catheter system as in claim 14, wherein the distal region and proximal region are formed from separate tubular members which are joined together.

20. A vascular imaging catheter system as in claim 14, wherein the proximal region including both lumens extends fully to the proximal end of the catheter body.

21. A vascular imaging catheter system as in claim 14, wherein the catheter body includes a first tubular member having at least one lumen and extending from the distal end to the proximal end of the catheter body and a second tubular member having at least one lumen and secured to the side of the first tubular member, wherein the two lumens converge at a junction spaced proximally from the distal end of the catheter body whereby the distal region lies distal to the junction and the proximal region lies proximal to the junction.

22. A vascular imaging catheter system as in claim 11, wherein the second tubular member extends fully to the proximal end of the catheter body.

23. A vascular imaging catheter system as in claim 11, wherein the second tubular member does not extend fully to the proximal end of the catheter body.

* * * * *